(12) United States Patent
Dang et al.

(10) Patent No.: US 6,607,554 B2
(45) Date of Patent: Aug. 19, 2003

(54) UNIVERSAL STENT LINK DESIGN

(75) Inventors: Kenny L. Dang, San Jose, CA (US); Andreina Gomez, Santa Clara, CA (US); Su-Wen Ueng, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/896,931

(22) Filed: Jun. 29, 2001

(65) Prior Publication Data

US 2003/0004566 A1 Jan. 2, 2003

(51) Int. Cl.⁷ .................................................. A61F 2/06
(52) U.S. Cl. ...................................................... 623/1.15
(58) Field of Search ................................ 623/1.15, 1.16, 623/1.11; 606/194, 195

(56) References Cited

U.S. PATENT DOCUMENTS

| | | | |
|---|---|---|---|
| 4,580,568 A | 4/1986 | Gianturco | |
| 5,104,404 A | 4/1992 | Wolff | |
| 5,383,892 A | 1/1995 | Cardon et al. | |
| 5,395,390 A | 3/1995 | Simon et al. | |
| 5,421,955 A | 6/1995 | Lau et al. | |
| 5,514,154 A | * 5/1996 | Lau et al. ................. | 606/108 |
| 5,549,663 A | 8/1996 | Cottone, Jr. | |
| 5,575,818 A | 11/1996 | Pinchuk | |
| 5,601,721 A | 2/1997 | Lukasiewicz et al. | |
| 5,695,516 A | 12/1997 | Fischell et al. | |
| 5,697,971 A | * 12/1997 | Fischell et al. ........... | 606/192 |
| 5,716,393 A | 2/1998 | Lindenberg et al. | |
| 5,735,893 A | 4/1998 | Lau et al. | |
| 5,741,327 A | 4/1998 | Frantzen | |
| 5,755,776 A | 5/1998 | Al-Saadon | |
| 5,776,161 A | * 7/1998 | Globerman ................ | 606/192 |
| 5,843,175 A | 12/1998 | Frantzen | |
| 5,902,332 A | 5/1999 | Schatz | |
| 5,911,732 A | 6/1999 | Hojeibane | |
| 5,911,754 A | 6/1999 | Kanesaka et al. | |
| 5,913,895 A | 6/1999 | Burpee et al. | |
| 5,931,867 A | 8/1999 | Haindl | |
| 5,935,162 A | 8/1999 | Dang | |
| 6,019,789 A | 2/2000 | Dinh et al. | |
| 6,042,597 A | 3/2000 | Kveen et al. | |
| 6,066,169 A | 5/2000 | McGuinness | |
| 6,068,656 A | * 5/2000 | Von Oepen ................ | 623/1.15 |
| 6,083,259 A | * 7/2000 | Frantzen .................... | 623/1.15 |
| 6,132,460 A | 10/2000 | Thompson | |
| 6,132,461 A | 10/2000 | Thompson | |
| 6,162,243 A | 12/2000 | Gray et al. | |
| 6,171,334 B1 | 1/2001 | Cox | |
| 6,190,403 B1 | 2/2001 | Fischell et al. | |
| 6,190,405 B1 | 2/2001 | Culombo et al. | |
| 6,217,608 B1 | 4/2001 | Penn et al. | |
| 6,334,870 B1 | * 1/2002 | Ehr et al. .................... | 623/1.1 |
| 6,364,900 B1 | * 4/2002 | Heuser ....................... | 623/1.11 |
| 6,375,677 B1 | * 4/2002 | Penn et al. ................. | 623/1.15 |
| 6,416,543 B1 | * 7/2002 | Hilaire et al. .............. | 623/1.16 |

FOREIGN PATENT DOCUMENTS

| | | |
|---|---|---|
| DE | 297 08 879 U1 | 7/1997 |
| DE | 299 04 817 | 5/1999 |
| EP | 0 888 757 A1 | 1/1999 |
| WO | WO 97/25937 | 7/1997 |
| WO | WO 98/22159 | 11/1997 |
| WO | WO 99/17680 | 4/1999 |

* cited by examiner

*Primary Examiner*—Michael J. Milano
*Assistant Examiner*—Sarah Webb
(74) *Attorney, Agent, or Firm*—Fulwider Patton Lee & Utecht, LLP

(57) ABSTRACT

The present invention provides an improved stent design for repairing a vessel. The stent design incorporates crimpable, short non-linear links which are flexible in three dimensions and which include flexible arms. The ability to accommodate both small deformations that occur during delivery and larger deformations that occur upon expansion within the vessel is enhanced without sacrificing stent crimp diameter. The link may incorporate a short flexible link with a perpendicular transition to provide added flexibility.

19 Claims, 4 Drawing Sheets

UNIVERSAL STENT LINK DESIGN

BACKGROUND OF THE INVENTION

The invention relates generally to a device for repairing vasculature, and more particularly to a design for stents that increases flexibility while still allowing the stent to be crimped to a small profile for delivery to an implant site.

Stents conventionally repair blood vessels that are diseased. Stents are generally hollow and cylindrical in shape and have terminal ends that are generally perpendicular to their longitudinal axis. In use, the conventional stent is positioned at the diseased area of a vessel and, after deployment, the stent provides an unobstructed pathway for blood flow.

Repair of vessels that are diseased can be particularly challenging since a stent used in the repair must be precisely positioned, provide adequate coverage of the disease and maintain vessel patency in order to allow adequate blood flow. Therefore, the stent must provide adequate coverage to the diseased portion of the vessel, without compromising blood flow, and extend to a point within and beyond the diseased portion. Where the stent provides coverage to the vessel at the diseased portion, yet extends into the vessel lumen at a bifurcation, for example, the diseased area is repaired, but blood flow may be compromised in other portions of the bifurcation. Unopposed stent elements may promote lumen compromise during neointimal formation and healing, producing restenosis and requiring further procedures. Moreover, by extending into the vessel lumen at a bifurcation, the stent may block access for further interventional procedures.

Recently, the art has taught the use of stents having a cylindrical body with rings aligned along a longitudinal axis, where each ring has a delivered diameter in which it is crimped or compressed tightly onto a balloon catheter or within a delivery catheter, and an implanted diameter where the stent is implanted in a vessel. Each ring includes a number of first peaks and one or more second peaks, with at least one second peak of each ring connected to a second peak of the adjacent ring by a link, the rings and links being made of struts. The first peaks are configured to spread apart to permit the rings to be expanded outwardly or to be compressed radially inwardly onto a delivery catheter. The second peaks and links provide longitudinal connection points between the rings.

By varying the number of rings and first peaks, the outward expansion of the various sections of the implanted stent can be varied and, thereby provide the required support at selected areas of the patient's lumen. Moreover, by varying the length and shapes of the links which connect the rings, the expandability, flexibility and degree of compression attainable may be customized. Flexibility of a stent is important with regard to both the ability of the stent to conform to the curvature of a tortuous artery after expansion and to the ability to maneuver the compressed stent through anatomy for delivery to the implant site. In particular, non-linear links may have undulating portions which have portions that are perpendicular to the longitudinal axis of the stent and which act as a hinge to enhance stent flexibility.

Although the undulating portions improve stent flexibility, they also may limit the extent of compression that may be achieved in the stent and therefore, result in a larger than desired delivery profile. Because the undulating portions include structure that extends generally perpendicular to the axis of the stent, in certain designs they will contact the adjacent first peaks when the stent is compressed, thereby limiting the degree of compression achievable. Additionally, the undulating portions may only accommodate small deformations that occur during stent delivery. Thus, the undulating portions may do little to accommodate large deformations occurring inside the vessel after the stent is expanded. Moreover, the undulating portions typically improve flexibility only in a longitudinal direction, but not in planes or directions perpendicular to the longitudinal axis of the stent.

Accordingly, what is needed is a stent with structure providing the stent with both desired flexibility and delivery profile. The present invention is directed to this need.

SUMMARY OF THE INVENTION

The invention provides an improved link design for cylindrical stents used to repair a vessel or whenever it is desired to increase or customized the flexibility of a stent. In one aspect, the stent of the present invention includes a link design which incorporates short non-linear links with flexible arms.

In a preferred embodiment, the stent of the present invention includes rings aligned along a longitudinal axis, where each ring has a delivered diameter in which it is crimped or compressed tightly, and an implanted diameter. Each ring includes struts defining a number of first peaks and one or more second peaks, with at least one second peak of each ring connected to a second peak of an adjacent ring by a link. The struts defining the first peaks are configured to spread apart to permit the rings to be expanded outwardly as well as to be compressed radially inwardly onto a delivery catheter. The second peaks and links provide longitudinal connection points between the rings.

In another aspect, at least some of the links which connect the second peaks are short non-linear links with flexible arms, the arms having gaps between them. The short links, which are flexible in the longitudinal direction as well as in planes or directions transverse or perpendicular to a longitudinal axis, accommodate small deformations which occur during stent delivery. Furthermore, the flexible arms accommodate large deformations, especially those that occur inside the vessel after the stent expands, while maintaining flexibility. Moreover, the gaps between the flexible arms facilitate greater compression of the stent for delivery. Added flexibility for delivery may be provided by adding one or more short flexible undulating portions generally perpendicular to a longitudinal axis of the stent.

The link design of the present invention may be incorporated into stents having various different link lengths as well as stents having sections with different link configurations. It is contemplated that the link design of the present invention may be employed whenever it is desired to increase the flexibility of a stent by incorporating flexible links between stent rings.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention embodies a stent, and link design therefor, for repairing a vessel or whenever it is desired to increase the flexibility of a stent having rings with first peaks and second peaks, the second peaks of adjacent rings connected by links. The stent link design of the present invention incorporates short non-linear links with flexible arms, the arms having gaps between them.

Figure 1:
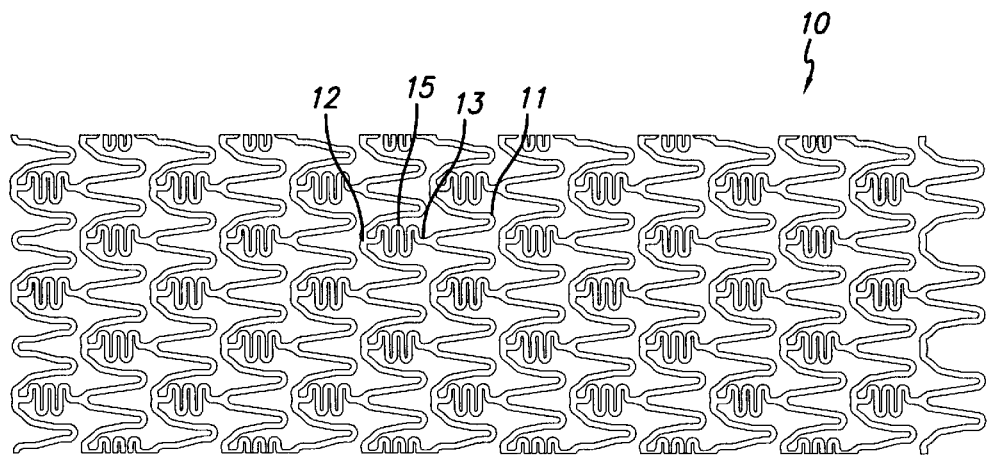
FIG. 1 is a flattened elevation view depicting a prior art stent in which every link is non-linear.
Figure 2:
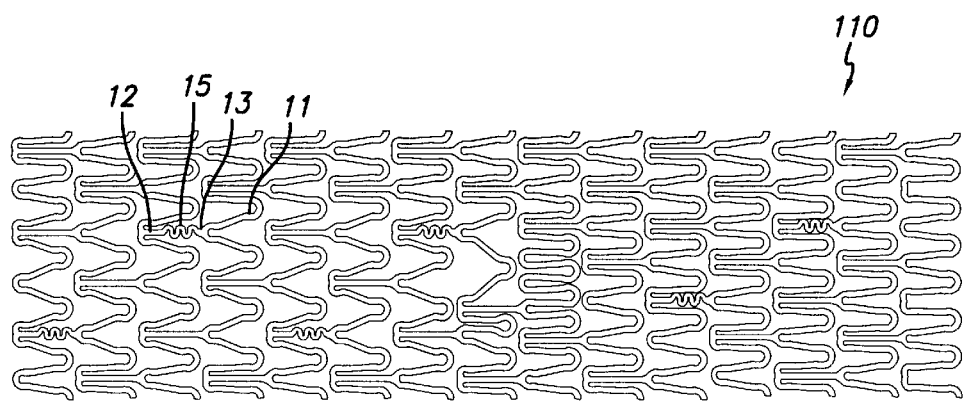
FIG. 2 is a flattened elevation view depicting a prior art stent in which not all the links are non-linear.

Prior art attempts at increasing the flexibility of stents by incorporating undulating portions in the links may have a detrimental effect on the compressibility of the stent and provide limited flexibility in directions other than that of a longitudinal axis of the stent, thereby accommodating only certain deformations or bending which occur during stent delivery. For example, FIGS. 1 and 2 depict prior art stents which include undulating portions in the links that connect the second peaks. FIG. 1 depicts a stent 10 having an undulating portion 15 in each link 13 between second peaks 12. FIG. 2 depicts a stent 110 in which only a portion of the links 13 between second peaks 12 have an undulating portion 15.

Note that the undulating portions 15 are generally perpendicular to a longitudinal axis of the stent 10 and, therefore, extend circumferentially a distance which is greater than a cross-sectional width of any portion of an individual link 13. The undulating portions 15 provide the stent with desired flexibility. However, the undulating portions 15 will contact the adjacent first peaks 11 when the stent is compressed for delivery, thereby decreasing the degree of compressibility achievable.

Figure 3A:
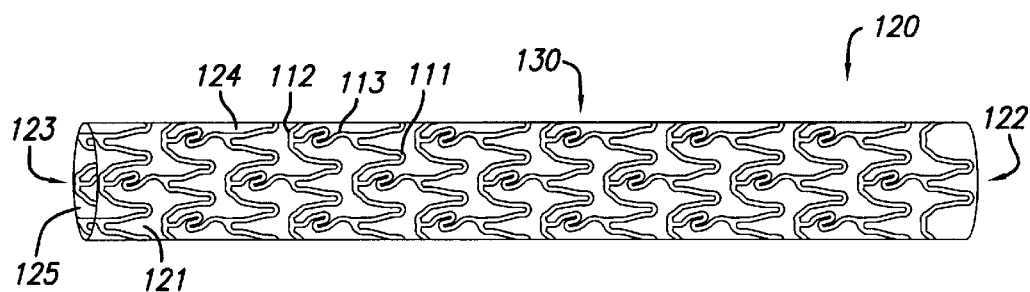
FIG. 3A is a perspective view depicting a preferred embodiment of the stent of the present invention in an unexpanded configuration.
Figure 3B:
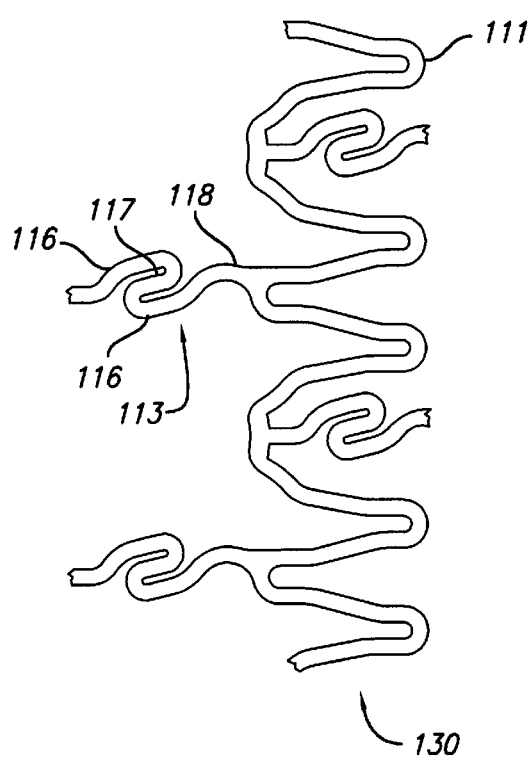
FIG. 3B is a flattened elevation view depicting a portion of the stent of the present invention.

FIGS. 3A and 3B depict a preferred embodiment of the present invention. The stent 120 has a cylindrical body 121 that includes a proximal end 122 and a distal end 123. The stent 120 can be self-expanding or balloon expanded. The stent 120 has an outer surface 124 which contacts the vascular wall, or walls defining any other body lumen, when implanted and an inner surface 125 through which blood flows when the stent 120 is expanded and implanted within a vessel. The stent 120 can be described as having a plurality connected rings 130 aligned along a common longitudinal axis of the stent. In one embodiment, each ring 130 has six first peaks 111 and has six oppositely opposed second peaks 112, though the rings can have fewer or more peaks for a particular purpose. The first peaks 111 are defined by struts configured to be spread apart to permit the stent 120 to be expanded to a larger diameter or compressed tightly toward each other for placement onto a catheter. In one aspect, the rings 130 are configured such that only three second peaks 112 of adjacent rings 130 are aligned. None of the first peaks 111 of adjacent rings are in phase or are aligned The aligned second peaks 112 of adjacent rings 130 are connected by a link 113. Further, the rings 130 are configured to expand into apposition with the walls of the vessel in which the stent 120 is implanted.

Each link 113 is further defined by flexible arms 116 which extend generally longitudinally, the arms having gaps 117 between them, and a short flexible link transition 118. In one embodiment, the flexible arms 116 form an S-shape or a pair of generally longitudinally extending and oppositely opposed open loops and operate to allow the stent to accommodate large deformations or translocations in directions transverse to a longitudinal axis of the stent which may occur as the stent is expended inside or delivered through a vessel. The gaps 117 between the flexible arms 116 allow greater compression of the stent for delivery by allowing the link 113 to be crimped to a smaller profile than is attainable with links having multiple undulating portions arranged generally perpendicular to a longitudinal axis of a stent. The short flexible link transition 118 defines curve or a plurality of curves directed generally transverse a longitudinal axis of the stent and provides additional flexibility by accommodating small deformations or translocations in a longitudinal direction during delivery. Accordingly, the link 113 of the present invention is flexible not only in the direction of the longitudinal axis of the stent, but also in directions transverse or perpendicular to a longitudinal axis of the stent to thereby provide greater overall flexibility.

The stent 120 typically is made from a metal alloy such as stainless steel, titanium, nickel-titanium (NiTi or nitinol of the shape memory or superelastic types), tantalum, cobalt-chromium, cobalt-chromium-vanadium, cobalt-chromium-tungsten, gold, silver, platinum, platinum-iridium or any combination of the foregoing metals and metal alloys. However, it is contemplated that the stent 120 may be made from any material and fabricated by any process known in the art.

FIGS. 4A–4E depict various embodiments of link designs. It is contemplated that any of the designs may be incorporated into the stent of the present invention. With respect to FIG. 4A, there is shown one preferred embodiment of the link design in which the link 213 is defined by flexible arms 216 which extend longitudinally, the arms having gaps 217 between them, and including a short flexible link with a relatively sharp transition 218 defining a space or gap 219, the same projecting generally transverse or perpendicular to a longitudinal axis of the stent. Note that the short flexible link has only one perpendicular transition which will crimp to approximately the same dimension as a circumferential dimension of the flexible arms 216 when the stent is compressed for delivery and which provides longitudinal flexibility and the ability to accommodate axial bending.

Figure 4A:
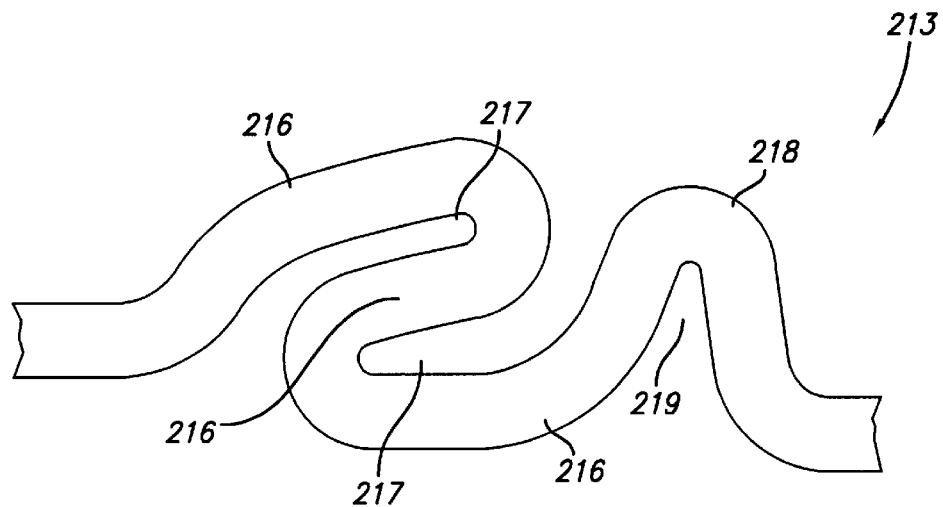
FIG. 4A is a schematic view of a preferred embodiment of a link design of the present invention having short flexible arms and a short undulating portion.
Figure 4B:
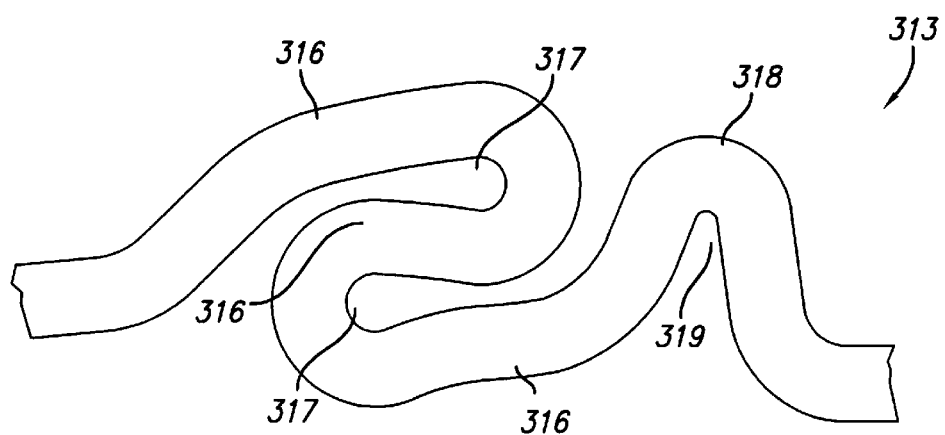
FIGS. 4B, 4C, and 4D are schematic views of alternate embodiments of the link design shown in FIG. 4A with varied dimensions for the flexible arms and short undulating portion.
Figure 4C:
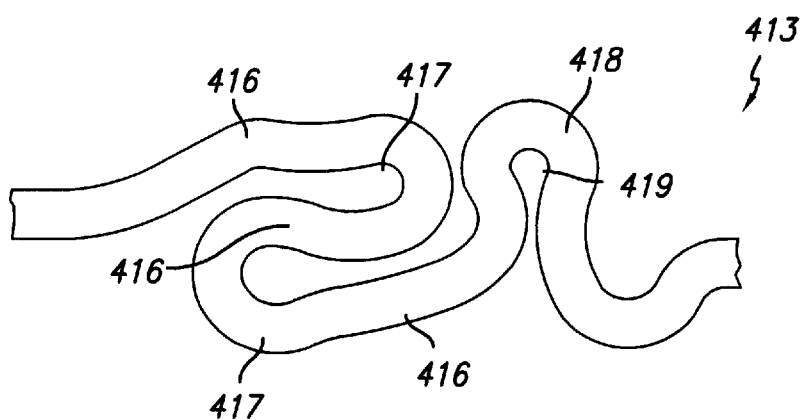
Figure 4D:
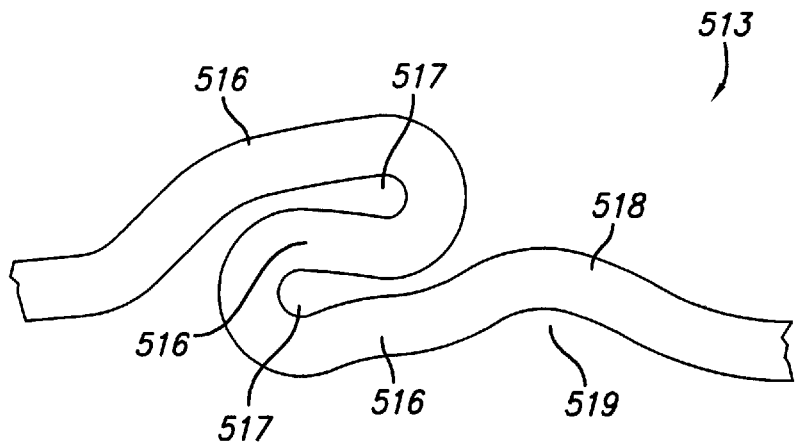

By varying the length, shape, and gap between the flexible arms 16 as well as the height, shape, and gap between struts defining the flexible link transition 18, the flexibility and compressibility of the link may be varied. FIGS. 4B, 4C, and 4D show alternate embodiments of the link 313, 413, 513 in which the dimensions of the flexible arms 316, 416, 516 and flexible link transitions 318, 418, 518 are varied. In particular, FIG. 4C depicts a link 413 having a flexible link transition 418 defining a gap 419 having a circumferential dimension approximating a circumferential dimension of the "S" formed by the flexible arms 416.

Figure 4E:
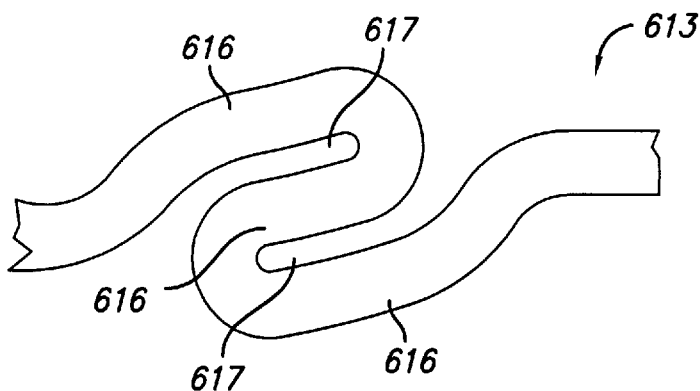
FIG. 4E is a schematic view of an alternate embodiment of the link design of the present invention having no undulating portion between flexible arms.

FIG. 4E depicts an alternate embodiment of the link design of the present invention. The link 613 is defined only by flexible arms 616. Since the link 613 is flexible in a plurality of directions or axes of the stent, the small deformations during stent delivery may be accommodated without a short flexible link 618.

It is contemplated that the stent may contain separate sections, each section having a different ring design chosen for the particular requirements of the vessel in which it is implanted such that not every link incorporates the same design. In fact, certain links can have a linear profile. It is further contemplated that not every link may incorporate the design of the present invention. It is also contemplated that the stent may have links with variable thickness or variable width struts in order to customize the radial strength of the stent, provide higher radiopacity under fluoroscopy, and enhance flexibility. The portions where the stent has the thinnest struts will be the most flexible. Variable thickness struts or variable width struts may be more radiopaque and may be positioned along the stent to help the physician position the stent during delivery and implantation in the vessel.

While particular forms of the invention have been illustrated and described, it will be apparent to those skilled in the art that various modifications can be made without departing from the scope of the invention. Accordingly, it is not intended that the invention be limited except by the appended claims.

What is claimed:

1. A stent, comprising:
    a cylindrical body having plurality of rings and a longitudinal axis; and
    at least one link connecting one of the plurality of rings to another of the plurality of rings, each link including a pa of flexible arms, the arms having a gap therebetween and connected such that they for an open loop which extends generally parallel to the longitudinal axis, the link further comprising a transition curve extending from one of the arms directed generally perpendicular to the longitudinal axis of the body wherein the transition curve is separate from he arm.

2. The stent of claim 1, at least one link further comprising at least three flexible arms connected to form at least a pair of open loops.

3. The stent of claim 1, wherein the link provides the stent with flexibility in three dimensions.

4. The stent of claim 2, wherein the stent is formed from a metal taken from a group including stainless steel, titanium, nickel-titanium, cobalt-chromium, cobalt-chromium-vanadium, cobalt-chromium-tungsten, gold, silver, platinum, or platinum iridium.

5. The stent of claim 1, wherein a circumferential dimension of the transition curve is approximately the same as a circumferential dimension of the flexible arms.

6. The stent of claim 1, wherein a circumferential dimension of the transition curve is less than a circumferential dimension occupied by the flexible arms.

7. The stent of claim 5, each ring further comprising six first peaks and six second peaks, the first peaks and second peaks of adjacent rings spaced such that only three second peaks of adjacent rings are aligned and the three aligned second peaks of adjacent rings are connected by one of the links.

8. The stent of claim 1, the link further comprising a plurality of transition curves directed transverse or generally perpendicular to the longitudinal axis of the body.

9. The stent of claim 1, wherein the body is self-expanding.

10. The stent of claim 1, wherein the body is balloon expandable.

11. The stent of claim 1, wherein the links are characterized by having a varying cross-sectional profile.

12. The stent of claim 1, wherein the arms generally define a S-shape.

13. A stent comprising:
    a cylindrical body having plurality of rings and a longitudinal axis;
    at least one link connecting one of the plurality of rings to another of the plurality of rings, each link including a plurality of flexible arms, the arms having gaps therebetween and connected such that they form a pair of open loops which extend generally parallel to the longitudinal axis, the link further comprising a transition curve extending from one of the arms directed generally perpendicular to the longitudinal axis of the body wherein the transition curve is separate from the arm; and
    each ring including six first peaks and six second peaks, the first peaks and second peaks of adjacent rings spaced such that only three second peaks of adjacent rings are aligned and the three aligned second peaks of adjacent rings are connected by one of the links.

14. The stent of claim 13, wherein the links provide the stent with flexibility in three dimensions.

15. The stent of claim 13, wherein the links are crimpable to thereby facilitate compressing the stent to a smaller diameter.

16. A stent comprising:
    a cylindrical body having plurality of rings and a longitudinal axis;
    at least one link connecting one of the plurality of rings to another of the plurality of rings, each link including a plurality of flexible arms, the arms having gaps therebetween and connected such that they form a pair of open loops which extend generally parallel to the longitudinal axis, the link further comprising a transition curve extending from one of the arms directed generally perpendicular to the longitudinal axis of the body wherein the transition curve is separate from the arm.

17. The stent of claim 16, wherein a circumferential dimension of the transition curve is less than a circumferential dimension occupied by the flexible arms.

18. The stent of claim 16, wherein the links are crimpable to thereby facilitate compressing the stent to a smaller diameter.

19. A method of treating body lumens using a stent having a plurality of adjacently arranged rings connected to each other by at least one link defined by open loops extending generally parallel to a longitudinal axis of the stent and a plurality of flexible arms, the link further including a transition curve extending from one of the arms directed generally perpendicular to the longitudinal axis of the stent wherein the transition curve is separate from the arm, comprising:
    applying a force to reduce a diameter of the stent;
    configuring the stent so that the link is compressed to a smaller dimension;
    placing the stent on a catheter;
    inserting the catheter within a body lumen; and
    deploying the stent within the body lumen.

* * * * *